US006852843B2

(12) United States Patent
Cavell et al.

(10) Patent No.: US 6,852,843 B2
(45) Date of Patent: Feb. 8, 2005

(54) PHOSPHORUS SUPPORTED CARBENE TRANSITION METAL COMPLEXES

(75) Inventors: Ronald G. Cavell, Edmonton (CA); Ruppa P. Kamalesh Babu, Edmonton (CA); Aparna Kasani, Edmonton (CA)

(73) Assignee: The Governors of the University of Alberta (CA)

( * ) Notice: Subject to any disclaimer, the term of this patent is extended or adjusted under 35 U.S.C. 154(b) by 0 days.

(21) Appl. No.: 10/356,884

(22) Filed: Feb. 3, 2003

(65) Prior Publication Data

US 2003/0158394 A1 Aug. 21, 2003

Related U.S. Application Data

(60) Division of application No. 09/770,979, filed on Jan. 26, 2001, now Pat. No. 6,538,115, which is a continuation of application No. 09/375,943, filed on Aug. 17, 1999, now abandoned, which is a continuation-in-part of application No. 09/174,782, filed on Oct. 19, 1998, now abandoned.

(51) Int. Cl.$^7$ ................................................. C07F 5/00
(52) U.S. Cl. ................................ 534/15; 568/8; 568/12
(58) Field of Search ........................... 534/15; 568/8, 568/9, 12, 16, 17; 556/9, 12, 13, 18, 19, 400

(56) References Cited

U.S. PATENT DOCUMENTS

| | | | |
|---|---|---|---|
| 5,502,128 A | 3/1996 | Flores et al. | |
| 5,557,023 A | 9/1996 | Somogyvari et al. | |
| 5,707,913 A | 1/1998 | Schlund et al. | |
| 6,060,568 A * | 5/2000 | Cavell et al. | 526/131 |
| 6,313,331 B1 * | 11/2001 | Cavell et al. | 556/18 |
| 6,476,245 B1 * | 11/2002 | Cavell et al. | 556/9 |
| 6,538,115 B2 * | 3/2003 | Cavell et al. | 534/15 |

FOREIGN PATENT DOCUMENTS

WO  WO 96/23010  8/1996

OTHER PUBLICATIONS

U. Zucchini, E. Albizzati and U. Giannini, Synthesis and Properties of Some Titanium and Zirconium Benzyl Derivatives, J. Organometal Chem., 26 (1971) 357–372.
Von R. Appel und I. Ruppert, Darstellung silyierter Alkylen–bisiminophosphorane und ihre Cyclisierung mit Phosphor (V)–fluoriden, Z.anor. allg. Chem. 406, 131–144 (1974).
Richard A. Andersen, Chloro– and Methyltris[(hexamethyldisilyl) amido]zirconium(IV) and –hafnium(IV), 1979 American Chemical Society, Inorganic Chemistry, vol. 18, No. 6, 1979, 1724–1725.
Michael D. Fryzuk, David H. McConville & Steven J. Rettig, Synthesis, structure and hydrogenation of n$^3$–benzyl diphosphine complexes of rhodium and iridium, J. or Organmettalic Chemistry, 445 (1993) 245–256.
George J.P. Britovsek, Vernon G. Gibson, Brian S. Kimberley, Peter J. Maddox, Stuart J. McTavish, Gregory A. Solan, Andrew J.P. White and David J. Williams, Novel Olefin polymerization catalysts based on iron and cobalt, Chem. Commun., 1998, p. 849.

* cited by examiner

Primary Examiner—Dameron L. Jones
(74) Attorney, Agent, or Firm—Kenneth H. Johnson

(57) ABSTRACT

The present invention relates to novel complexes of (transition) metals containing ligands having phosphorus centers supporting a carbene atom or heteroalkane radical bonded to the (transition) metal.

35 Claims, No Drawings

PHOSPHORUS SUPPORTED CARBENE TRANSITION METAL COMPLEXES

This is a division of application Ser. No. 09/770,979, filed Jan. 26, 2001, now U.S. Pat. No. 6,538,115, which is a continuation of application Ser. No. 09/375,943, filed Aug. 17, 1999, now abandoned, which is a continuation-in-part of application Ser. No. 09/174,782, filed Oct. 19, 1998, now abandoned.

FIELD OF THE INVENTION

The present invention relates to novel complexes of metals preferably transition metal and to processes for producing such complexes. The complexes contain at least one phosphorus center, and a carbon atom or an alkyl radical bonded to the metal to form a carbene or metal heteroatom alkenyl bond.

BACKGROUND OF THE INVENTION

Currently there is increasing interest in complexes of transition metals having a novel structure. Potentially such compounds could have significant use in a number of applications such as chemical processing, herbicides, pesticides and possibly medical fields.

Recently there has been significant interest in the catalyst of Brookhart et al which may activate later transition metals in a polymerization process. Such complexes are disclosed, for example, in World patent application 96/23010 jointly in the names of The University of Carolina at Chapel Hill and E.I. DuPont published Aug. 1, 1996. The Brookhart et al patent application does not teach the complexes of the present invention.

The recent paper (Chem. Comm (1998) p. 849) by the coworkers of Gibson at Imperial College UK (and BP) teach complexes having a novel structure that is dissimilar to the complexes of the present invention. It is postulated the complexes of Gibson will have utility in the polymerization of certain monomers such as alpha olefins.

There has been a great deal of work recently by both Exxon in the field of metallocene chemistry and by the Dow Chemical Company in single site constrained geometry complexes. As far as applicant has been able to determine none of the chemistry proposed by either Exxon or Dow contain a carbene atom or a constrained alkyl carbon bonded to a transition metal.

There are several patents relating to amidinato complexes of transition metals which are suitable for the polymerization of various olefins. U.S. Pat. No. 5,502,128 issued Mar. 26, 1996, assigned to the University of Massachusetts, teaches such complexes may be used to polymerize vinyl aromatic monomers; and U.S. Pat. No. 5,707,913 issued Jan. 13, 1998, assigned to BASF, teaches such compounds may be used polymerize olefins. Neither of these patents disclose complexes of the structure of the present invention.

U.S. Pat. No. 5,557,023 issued September, 1996, teaches the use of some complexes of transition metals to oligomerize lower alpha olefins such as ethylene to higher olefins such as hexene and the like. The complexes of the patent do not contain a carbene atom or substituted carbon bonded to the transition metal.

Applicant has been unable to identify any prior art disclosing the complexes of the present invention. In short the complexes of the present invention represent a novel chemistry having potential applications in many fields.

SUMMARY OF THE INVENTION

The present invention provides a complex having the formula:

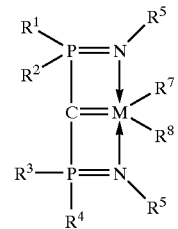

wherein M is a metal atom; $R^1$, $R^2$, $R^3$ and $R^4$ are independently selected from the group consisting of a hydrogen atom, a saturated or unsaturated straight chained, branched or cyclic hydrocarbyl radical which is unsubstituted or substituted by one or more substituents selected from the group consisting of a halogen atom and a $C_{1-6}$, most preferably a $C_{1-4}$ alkyl radical; $R^7$ and $R^8$ are independently selected from the group consisting of a hydrogen atom, a halogen atom, an amide —$NR^1R^2$, imide =$NR^1$, alkoxide or aryl oxide group —$OR^1$, and an —$OSi(R^1)_3$ group where $R^1$ and $R^2$ are defined above, and a saturated or unsaturated straight chained, branched or cyclic hydrocarbyl radical which are unsubstituted or substituted by a halogen atom or a $C_{1-6}$ alkyl radical or a Lewis base (neutral coordinating ligands) which may contain a donor heteroatom including but not limited to ethers, tertiary amines, tertiary phosphines and cyclic amines; and each $R^5$ is independently selected from the group consisting of radicals selected from the group consisting of saturated and unsaturated straight chained, branched and cyclic hydrocarbyl radicals, preferably $C_{1-15}$ saturated or unsaturated straight chained, branched or cyclic hydrocarbyl radicals most preferably $C_{1-8}$ straight or branched alkyl radicals and $C_{6-12}$ cyclic aliphatic or aromatic radical; radicals of the formula $Si(R^6)_3$ wherein each $R^6$ is independently selected from the group consisting of saturated or unsaturated straight chained, branched or cyclic hydrocarbyl radicals, preferably $C_{1-10}$ saturated or unsaturated straight chained, branched or cyclic hydrocarbyl radicals; and radicals of the formula III:

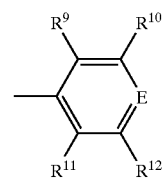

wherein $R^9$, $R^{10}$, $R^{11}$ and $R^{12}$ are independently selected from the group consisting of a hydrogen atom, a fluorine atom, a $NO_2$ radical, a $C_{1-6}$ alkyl radical, and a $C_{8-12}$ aryl radical and E is an endocyclic nitrogen atom or a C—CN group.

The present invention provides a complex dilithium salt of the formula II:

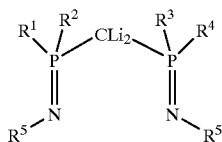

wherein $R^1$, $R^2$, $R^3$ and $R^4$ are independently selected from the group consisting of a hydrogen atom, a saturated or unsaturated straight chained, branched or cyclic hydrocarbyl radical which is unsubstituted or substituted by one or more substituents selected from the group consisting of a halogen atom and a $C_{1-6}$, most preferably a $C_{1-4}$ alkyl radical; and each $R^5$ is independently selected from the group consisting of radicals selected from the group consisting of a saturated or unsaturated straight chained, branched or cyclic hydrocarbyl radicals preferably $C_{1-15}$ saturated or unsaturated straight chained, branched or cyclic hydrocarbyl radicals, most preferably $C_{1-8}$ straight or branched alkyl radicals and $C_{6-12}$ cyclic aliphatic or aromatic radicals; radicals of the formula $Si(R^6)_3$ wherein each $R^6$ is independently selected from tho group consisting of saturated or unsaturated straight chained, branched or cyclic hydrocarbyl radicals, preferably $C_{1-10}$ saturated or unsaturated straight chained, branched or cyclic hydrocarbyl radicals; radicals of the formula III:

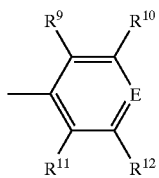

wherein $R^9$, $R^{10}$, $R^{11}$ and $R^{12}$ are independently selected from the group consisting of a hydrogen atom, a fluorine atom, a $NO_2$ radical, a $C_{1-6}$ alkyl radical, and a $C_{8-12}$ aryl radical and E is an endocyclic nitrogen atom or a C—CN group.

The present invention also provides processes for the production of the above complexes comprising either:

(A) reacting a compound of the formula I:

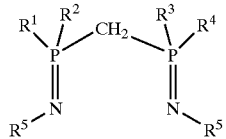

wherein $R^1$, $R^2$, $R^3$, $R^4$ and $R^5$ are as defined above, with a compound of the formula $M(X)_s(Y)_t(L)_n$ wherein M is as defined above, X is independently selected from a group consisting of an alkyl radical, preferably having from 1 to 10 carbon atoms which is unsubstituted or substituted by a $C_{1-4}$ alkyl radical or a $C_{6-10}$ aryl (e.g. benzyl) radical, a silylated amido or imido complex —N(Si(R^6)_3)_2 or =N(Si(R^6)_3 where $R^6$ is defined above, or imido =NR radicals where R is a $C_{1-10}$ alkyl or a $C_{6-10}$ aryl radical, Y is selected from the group consisting of a halogen atom, an alkoxy radical preferably having from 1 to 10 carbon atoms and aryloxy radicals preferably having from 6 to 10 carbon atoms, and the sum of s and t equal the valence of the transition metal M and provided that at least two of the X and Y groups can be eliminated from the molecule, L is a Lewis base as defined above and n is from 0 to 3; in a $C_{5-12}$ hydrocarbyl solvent or a $C_{2-10}$ ether solvent at a temperature from 20° C. to 150° C.; or (B) reacting a compound of the formula II:

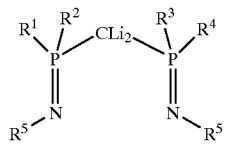

wherein $R^1$, $R^2$, $R^3$, $R^4$ and $R^5$ are as defined above, with a compound of the formula $M(X)_t(Y)_s(L)_n$ wherein M, L, s, t and n are as defined above, X and Y are independently selected from a group consisting of an alkyl, preferably having from 1 to 10 carbon atoms which is unsubstituted or substituted by a $C_{1-4}$ alkyl radical or a $C_{6-10}$ aryl (e.g. benzyl) radical, a silylated amido or imido complex —N(Si(R^6)_3)_2 or =N(Si(R^6)_3 where $R^6$ is defined above, or imido =NR radicals where R is a $C_{1-10}$ alkyl or a $C_{6-10}$ aryl radical, a halogen atom, an alkoxy radical preferably having from 1 to 10 carbon atoms and aryloxy radical preferably having from 6 to 10 carbon atoms, and the sum of s and t equal the valence of the transition metal M and provided that at least two of the X and Y groups can be eliminated from the molecule, in a $C_{5-12}$ hydrocarbyl solvent or a $C_{2-10}$ ether solvent at a temperature from 20° C. to 150° C.

The present invention further provides a process comprising reacting a complex of the formula:

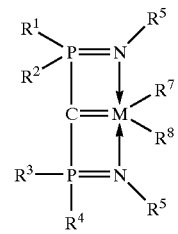

wherein $R^1$, $R^2$, $R^3$, $R^4$ and $R^5$ are as defined above, and at least one of $R^7$ and $R^8$ are halogen atoms and the other may be a Lewis base as defined above, with a Grignard reagent or an alkylating or alkoxylating agent.

DETAILED DESCRIPTION

In the complexes of the present invention the metal may be any transition metal. It may be an early transition metal such as Y, Ti, V, Zr, Hf or Cr or it may be a later transition metal such as Ni, Pd, Pt, group 11 or 12, a post transition metal (Zn) or a lanthanide group metal, preferably Sm. Preferably the transition metal will be selected from group 3 through 10 (formerly group IIIB through VIII) of the periodic table.

The transition metal precursor $M(X)_s(Y)_t(L)_n$ must contain at least two X or Y substituents which are eliminated in reaction with the compounds of formula I or formula II.

In accordance with the present invention $R^1$, $R^2$, $R^3$ and $R^4$ may be independently selected from the group consisting of a hydrogen atom, a saturated or unsaturated straight chained, branched or cyclic hydrocarbyl radical which is unsubstituted or substituted by one or more substituents selected from the group consisting of a halogen atom and a $C_{1-6}$, most preferably a $C_{1-4}$ alkyl radical. Preferably, the hydrocarbyl radicals may be selected from the group consisting of a $C_{1-10}$, preferably $C_{1-8}$, most preferably $C_{1-6}$ straight chained, branched or cyclic alkyl radicals which radicals may be unsubstituted or further substituted, preferably by not more than three substituents selected from the group consisting of $C_{1-4}$ alkyl radicals or a halogen atom, preferably either F or Cl. Additionally, substituents $R^1$, $R^2$, $R^3$ and $R^4$ may be independently selected from the group consisting of $C_{5-14}$ aromatic radicals which radicals are unsubstituted or substituted by up to n−1, wherein n is the number of carbon atoms in the aromatic radical, substituents selected from the group consisting of a halogen atom, preferably F or Cl, a $C_{1-6}$, most preferably a $C_{1-4}$ alkyl radical or an amido radical which is unsubstituted or substituted by up to two $C_{1-6}$, preferably $C_{1-4}$ alkyl radicals.

The substituents $R^1$, $R^2$, $R^3$ and $R^4$ may be selected from the group consisting of a hydrogen atom, a fluorine atom, a chlorine atom, a methyl radical, an ethyl radical, a propyl radical, a butyl radical, a tertiary butyl radical, and a phenyl radical.

In some embodiments of the present invention $R^1$ and $R^2$ may be the same. In a further embodiment $R^3$ and $R^4$ may be the same. In a further embodiment of the present invention all of $R^1$, $R^2$, $R^3$ and $R^4$ may be the same.

In the present invention $R^7$ and $R^8$ may be independently selected from the group consisting of a hydrogen atom, a halogen atom, an amide radical —$NR^1R^2$, imide =$NR^1$, alkoxide or aryl oxide group —$OR^1$, and an —O—$Si(R^1)_3$ group where $R^1$ and $R^2$ are defined above; and a saturated or unsaturated straight chained, branched or cyclic hydrocarbyl radical which are unsubstituted or substituted by a halogen atom, a $C_{1-6}$ alkyl radical or a Lewis base (neutral coordinating ligands) which may contain a donor heteroatom including but not limited to ethers, tertiary amines, tertiary phosphines and cyclic amines. The hydrocarbyl radical may be a straight chained or branched $C_{1-10}$ alkyl radical which may be unsubstituted or substituted by a F or Cl atom or up to three $C_{1-6}$, preferably $C_{1-4}$ alkyl radicals. The hydrocarbyl radical may be selected from the group consisting of $C_{5-14}$ aromatic radicals which radicals are unsubstituted or substituted by up to n-1, wherein n is the number of carbon atoms in the aromatic radical, substituents selected from the group consisting of a halogen atom, preferably F or Cl, a $C_{1-6}$, most preferably a $C_{1-4}$ alkyl radical or an amido radical which is unsubstituted or substituted by up to two $C_{1-6}$, preferably $C_{1-4}$ alkyl radicals. Some suitable Lewis bases (neutral coordinating ligands) comprise one or more donor heteroatoms including but not limited to $C_{1-6}$ alkyl ethers, $C_{4-8}$ cyclic ethers, $C_{1-6}$ tertiary amines and cyclic nitrogen aromatics from 4 to 8 carbon atoms such as pyridine or tertiary $C_{1-10}$ phosphines. In one embodiment of the invention at least one of $R^7$ and $R^8$ may be $C_{5-13}$ ligand containing a 5-membered carbon ring having delocalized bonding within the ring and typically being bound to the metal through covalent $\eta^5$-bonds such as cyclopentadienyl, indenyl or fluorenyl ligands which are unsubstituted or up to fully substituted by a halogen atom, preferably chlorine or fluorine, a $C_{1-4}$ alkyl radical or an amido radical which is unsubstituted or substituted by up to two $C_{1-4}$ alkyl radicals.

In accordance with the present invention each $R^5$ is independently selected from the group consisting of radicals of a saturated or unsaturated straight chained, branched or cyclic hydrocarbyl radical, preferably $C_{1-15}$ saturated or unsaturated straight chained, branched or cyclic hydrocarbyl radicals, most preferably a $C_{1-8}$ straight or branched alkyl radical and a $C_{6-12}$ cyclic aliphatic or aromatic radical; radicals of the formula $Si(R^6)_3$ wherein each $R^6$ is independently selected from the group consisting of saturated or unsaturated straight chained, branched or cyclic hydrocarbyl radicals, preferably $C_{1-10}$ saturated or unsaturated straight chained, branched or cyclic hydrocarbyl radicals preferably $C_{1-10}$ saturated or unsaturated straight chained, branched or cyclic hydrocarbyl radicals; radicals of the formula III:

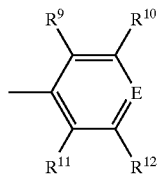

wherein $R^9$, $R^{10}$, $R^{11}$ and $R^{12}$ are independently selected from the group consisting of a hydrogen atom, a fluorine atom, a $NO_2$ radical, a $C_{1-6}$ alkyl radical, and a $C_{8-12}$ aryl radical and E is an endocyclic nitrogen atom or a C—CN group.

Each $R^5$ radical may be selected from the group consisting of radicals of the formula $Si(R^6)_3$ wherein each $R^6$ is independently selected from the group consisting of saturated or unsaturated straight chained, branched or cyclic hydrocarbyl radicals, preferably $C_{1-10}$ saturated or unsaturated straight chained, branched or cyclic hydrocarbyl radicals. Most preferably R is selected from $C_{1-8}$, preferably $C_{1-6}$, most preferably $C_{1-4}$ alkyl radicals. Suitable alkyl radicals include methyl, ethyl, propyl and butyl radicals. In a preferred embodiment of this aspect of the invention each $R^6$ radical is the same.

Each $R^5$ radical may be selected from the group consisting of radicals of the formula III:

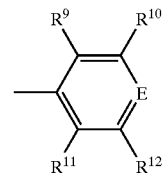

wherein $R^9$, $R^{10}$, $R^{11}$ and $R^{12}$ are independently selected from the group consisting of a hydrogen atom, a fluorine atom, a $NO_2$ radical, a $C_{1-6}$ alkyl radical, and a $C_{8-12}$ aryl radical and E is an endocyclic nitrogen atom or a C—CN group. Such radicals includes the 4-cyanotetrafluorophenyl radical.

Independently each $R^5$ radical may selected from the group consisting of consisting of saturated or unsaturated straight chained, branched or cyclic hydrocarbyl radicals, preferably $C_{1-15}$ saturated or unsaturated straight chained, branched or cyclic hydrocarbyl radicals most preferably a $C_{1-8}$ straight or branched alkyl radical and a $C_{6-12}$ cyclic aliphatic or aromatic radical. Some hydrocarbyl radicals include methyl, ethyl, butyl, phenyl and adamantyl radicals.

The compounds of the present invention may be prepared by reacting a compound of the formula I as defined above wherein $R^1$, $R^2$, $R^3$, $R^4$ and $R^5$ are as defined above with a compound of the formula $M(X)_s(Y)_t(L)_n$ wherein M is as defined above, X is independently selected from a group consisting of an alkyl radical, preferably having from 1 to 10 carbon atoms which is unsubstituted or substituted by a $C_{1-4}$ alkyl radical or a $C_{6-10}$ aryl (e.g. benzyl) radical, a silylated amido or imido complex —$N(Si(R^6)_3)_2$ or =$N(Si(R^6)_3)_2$ where $R^6$ is defined above, or imido =NR radicals where R is a $C_{1-10}$ alkyl radical or a $C_{6-10}$ aryl radical, Y is a halogen atom, a alkoxy radical preferably having from 1 to 10 carbon atoms and aryloxy radical preferably having from 6 to 10 carbon atoms, and the sum of s and t equal the valence of the transition metal M and provided that at least two of the X and Y groups can be eliminated from the molecule, in a $C_{5-12}$ hydrocarbyl solvent or a $C_{2-10}$ ether solvent at a temperature from 20° C. to 150° C. Suitably X and Y radicals include but are not limited to bis(trimethylsilyl) amido; benzyl; and suitable Lewis bases include, but are not restricted to diethyl ether or tetrahydrofuran. L is a Lewis base (neutral coordinating ligands) which may contain a donor heteroatom including but not limited to ethers, tertiary amines, tertiary phosphines and cyclic amines. Some suitable Lewis bases (neutral coordinating ligands) comprise one or more donor heteroatoms including but not limited to $C_{1-6}$ alkyl ethers, $C_{4-8}$ cyclic ethers, $C_{1-6}$ tertiary amines, cyclic nitrogen aromatics from 4 to 8 carbon atoms such as pyridine, or tertiary $C_{1-10}$ phosphines, and n may range from 0 to 3. The final form of the compound may retain some of the Lewis bases components defined as L or a similar species obtained from the reaction solvent. Alternatively the compound above of the formula I may be reacted with two moles of alkyl lithium reagent to prepare the dilithio derivative of the formula $\{R^1R^2\{N(R^5)\}PC(Li)_2PR^3R^4\{N(R^5)\}\}$:

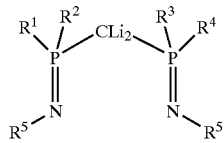

(formula II (preferably $R^5$ is $Si(R^6)_3$ wherein $R^6$ is a $C_{1-4}$ alkyl radical) which in turn can be reacted with metal halide or alkyl halide precursors $M(X)_s(Y)_t(L)_n$ as defined above containing at least two halogen atoms as replaceable substituents in the X and Y group.

The complexes of the present invention wherein the $R^7$ and $R^8$ are halogens and may be alkylated or alkoxylated by reacting with suitable alkylating agents such as LiR or RMgX or alkoxylating agent which is an alkali alkoxide (e.g. $M^2OR$ where $M^2$ is selected from the group consisting of alkali metals, preferably sodium). In the alkylating or alkoxylating agent, the alkyl or alkoxide radical is as defined in $R^7$ and $R^8$ above.

Some hydrocarbon solvents include $C_{5-12}$ hydrocarbons which may be unsubstituted or substituted by $C_{1-4}$ alkyl group, such as pentane, hexane, heptane, octane, cyclohexane, methylcyclohexane and hydrogenated naphtha. An additional solvent is Isopar E ($C_{8-10}$ aliphatic solvent, Exxon Chemical Co.). The solvent may be aromatic such as benzene, toluene or xylene. The solvent may also be a simple or branched ether in which the alkyl radicals may contain from 1 to 10 carbon atoms or a polyether thereof such as diethyl ether and diglyme. The product is recovered using conventional procedures illustrated in the examples. The reaction may be carried out from room temperature (20° C.) to about 150° C.

The present invention will be illustrated by the following non-limiting examples in which, unless otherwise specified, part means parts by weight (e.g. grams) and per cent means weight per cent.

Synthesis of Ligands and Metal Carbene Complexes
General Experimental Conditions All experimental manipulations were performed under rigorously anaerobic conditions using Schlenk techniques or an argon-filled glovebox with an efficient recirculator. Solvents were dried and distilled under argon prior to use. Hexane and toluene were distilled from Na—K and Na respectively. NMR solvents benzene-$d_6$ and toluene-$d_8$ were freshly vacuum transferred from Na—K. Commercial (Aldrich) supplies of dppm, $Me_3SiN_3$, $ZrCl_4$ and $HfCl_4$ were used as obtained. NMR spectra were recorded using Bruker® WH-200, 300 and 400 spectrometers with reference to the deuterium signal of the solvent employed. The $^1H$ NMR chemical shifts are reported in ppm from external $Me_4Si$ and the $^{31}P$ NMR spectra are reported in ppm from external 85% $H_3PO_4$. Positive values reflect shifts downfield. Infrared spectra were recorded on a Nicolet® 7199 infrared spectrometer.

Preparation of Ligands
Preparation of $CH_2[Cy_2P=NSiMe_3]_2$

To a solution of dcpm, $\{Cy_2P\}_2CH_2$, (literature preparation: Fryzuk, M. D.; McConville, D. H.; Rettig, S. J. *J. Organomet. Chem.* 1993, 445, 245–256.}(3.97 g, 9.72 mmol) in 60 mL of toluene was added trimethylsilyl azide (6 mL, 45.79 mmol) with stirring. The solution was heated to reflux at 110° C. for 48 hours. Solvent was evaporated under vacuum to obtain microcrystalline solid which was washed twice with hexane and dried (Yield: 4.85 g, 85.6%). IR (Nujol mull): 2666 w, 2653 w, 1449 s, 1376 m, 1348 m, 1302 s, 1264 s, 1244 s, 1233 s, 1209 m, 1173 m, 1154 m, 1119 w, 1078 w, 1045 w, 1028 w, 1004 m, 913 w, 896 m, 852 s, 827 s, 787 s, 776 s, 751 s, 675 m, 663 m, 633 m, 571 w, 526 m. $^1H$ NMR ($C_6D_6$): δ 1.95 (b. t, 4 H, CH-Cy methine), 1.7 (m, $CH_2$-Cy methylene), 1.62 (d, $^2J_{PH}$=12.2 Hz, 2 H, $PCH_2P$ methylene), 1.40–1.05 (m, $CH_2$-Cy methylene), 0.38 (s, 18 H, $CH_3Si$ methyl). $^{13}C\{^1H\}$ NMR ($C_6D_6$): δ 39.5 (m, 4 C, CH-Cy, methine), 27.1 (s, 4 C, para Cy), 27.0 (s, 8 C, ortho Cy), 26.8 (s, 4 C, meta Cy), 26.5 (s, 4 C, meta Cy), 21.6 (t, $^1J_{PC}$=61.6 Hz, 1 C, $PCH_2P$ methylene), 5.3 (s, 6 C, $CH_3Si$). $^{13}\{^1H, ^{31}P\}$ NMR ($C_6D_6$): δ 39.5 (s, 4 C, CH-Cy, methine), 27.1 (s, 4 C, para Cy), 27.0 (s, 8 C, ortho Cy), 26.8 (s, 4 C, meta Cy), 26.5 (s, 4 C, meta Cy), 21.6 (s, 1 C, $PCH_2P$ methylene), 5.3 (s, 6 C, $CH_3Si$). $^{31}P\{^1H\}$ NMR ($C_6D_6$): δ 14.6 (2 P). Analysis calculated for $C_{31}H_{64}N_2P_2Si_2$: C, 63.87; H, 11.06; N, 4.81. Found: C, 63.55; H, 11.22; N, 4.63.

Preparation of $CH_2[Ph_2P=NSiMe_3]_2$

As described in the literature {Appel, R.; Ruppert, I. *Z. anorg. allg. Chem.* 1974, 406, 131–144.}.

Preparation of $CH_2(Ph_2P=NAd)_2$

Adamantyl azide (1.66 g, 9.37 mmol) was added to a solution of bis(diphenylphosphino)methane (dppm) (1.80 g, 4.68 mmol) in 60 mL of toluene. The mixture was heated to reflux at 110° C. for 2 days. The solution was then cooled to room temperature, concentrated to about 20 mL, and maintained at −15° C. to yield, after about 12 hours, a microcrystalline solid which was filtered and dried (Yield: 2.56 g, 80%). $^1H$ NMR (toluene-$d_8$): δ 7.87 (b. s, 8 H, ortho-Ph), 7.05 (b. s, 12 H, meta and para-Ph), 3.48 (b. t, 2 H, $CH_2$), 1.99 (b.s, 3 H, CH-Ad), 1.93 (b. s, 6 H, $CH_2$-Ad), 1.59 (b. s, 6 H, $CH_2$-Ad). $^{31}P\{^1H\}$ NMR (toluene-$d_8$): δ−15.4 (s). Analysis calculated for $C_{45}H_{52}N_2P_2$: C, 79.15; H, 7.68; N, 4.10. Found: C, 78.58; H, 7.93; N, 4.03.

Preparation of $Me_3Si=NPPh_2CH_2Ph_2P=NC_6F_4$-p-CN

To a solution of bis(diphenylphosphino)methane (dppm) (11.17 g, 20 mmol) in dichloromethane a solution of pentafluorobenzonitrile (4.05 g, 21 mmol) in dichloromethane (35 mL) was added at room temperature. Immediately the solution turned yellow and after stirring for 12 hours became orange. The solvent was completely removed in vacuo leaving the slightly orange colored crude product which was recrystallized from acetonitrile giving the pure ligand (Yield: 10.28 g, 78%; white cubic crystals; mp 198–200° C.). Analysis calculated for $C_{35}H_{31}F_4N_3P_2Si$: C, 63.77; H, 4.69; N, 6.36. Found: C, 63.01; H, 4.70; N, 6.46. MS (EI, m/z): 659 ($M^+$). $^1H$ NMR ($CD_2Cl_2$): phenyl rings δ 7.80 to 7.74 ppm, 7.57 to 7.29 ppm (m, 20H); $PCH_2$ P methylene, δ 3.75 ppm ('t', 2H, $^2J_{HP}$ 13.39 Hz); $Me_3$ Si methyl δ−0.29 ppm (s, 9H). $^{19}F\{^1H\}$ NMR ($CDCl_2$): ortho δ−140.17 ppm (m, 2F); meta δ−153.32 ppm (m, 2F). $^{29}Si\{^1H\}$ NMR ($CDCl_2$), δ−10.59 ppm (d, $^2J_{SiP}$ 20.49 Hz).

Preparation of $\{Li_2C\{Ph_2P=NSiMe_3\}_2\}$

Colorless crystalline bis(diphenylphosphinomethyl-trimethysilylimino) methane $H_2C\{Ph_2P=NSiMe_3\}_2$ (1.0 g, 1.79 mmol) was dissolved in 20 mL of toluene. To this toluene solution, PhLi (0.30 g, 3.59 mmol) was added with stirring. The reaction mixture was stirred at room temperature for 3 days. Approximately 100 mg of colorless solid was removed by filtration. The clear solution was reduced to one-half volume and allowed to stand at room temperature for 48 hours whereupon colorless crystals deposited. (Yield:

0.62 g, 60.7%). IR (Nujol mull): 1434 m, 1244 s, 1190 s, 1174 m, 1101 s, 1067 s, 852 s, 832 s, 764 m, 747 m, 725 m, 709 m, 696 s, 675 w, 663 w, 646 s, 618 w, 606 w, 539 s, 512 m. $^1$H NMR ($C_6D_6$): δ 7.53–7.49 (m, phenyl), 7.04–6.93 (m, phenyl), 0.04 (s, $CH_3Si$ methyl). $^{13}C\{^1H\}$ NMR ($C_6D_6$): δ 139.0 (m, 4 C, ipso phenyl), 131.0 (t, $^2J_{PC}$=4.5 Hz, 8 C, ortho phenyl), 129.0 (s, 4 C, para phenyl), 127.8 (s, 8 C, meta phenyl), 4.4 (s, 6 C, $CH_3Si$). $^{31}P\{^1H\}$ NMR ($C_6D_6$): δ 13.7 (2 P). Analysis calculated for $C_{31}H_{38}Li_2N_2P_2Si_2$: C, 65.25; H, 6.71; N, 4.91. Found: C, 65.27; H, 6.69; N, 4.60.

Preparation of Metal Carbene and Related Derivatives

Preparation of [$ZrCl_2\{C(Cy_2P=NSiMe_3)_2\}$]

[$ZrCl_2\{N(SiMe_3)_2\}_2$] (0.5 g, 1.04 mmol) {literature preparation: Andersen, R. A. Inorg. Chem. 1979, 18, 1724–1725} was dissolved in 15 mL of toluene by stirring. Solid bisimine ligand, $CH_2(Cy_2P=NSiMe_3)_2$ (0.604 g, 1.04 mmol) was added to the solution which was then heated to reflux at 130° C. for five days. The pale yellow solution was concentrated to about 10 mL and left at room temperature for 24 hours whereupon pale yellow crystals formed which were isolated by filtration (0.42 g). The mother liquor was concentrated 5 mL hexane added and the total mixture was cooled to –15° C. for 24 hours which yielded a second crop of product (0.15 g). (Yield: 0.57 g, 75.2%). IR (Nujol mull): 1447 s, 1403 w, 1377 m, 1356 w, 1321 s, 1258 s, 1246 s, 1200 w, 1192 m, 1176 m, 1167 w, 1111 m, 1049 b.s, 998 m, 915 w, 887 m, 837 s, 779 m, 769 s, 753 m, 746 s, 679 m, 651 s, 634 m, 609 s, 551 s, 509 w, 495 m, 484 w, 465 w. $^1$H NMR ($C_6D_6$): δ 2.1–1.1 (b. m, 40 H, $CH_2$-Cy methylene), 1.76 (m, 4 H, CH-Cy methine) (as assigned from a $^1$H-$^{13}$C HMQC expt.), 0.51 (s, 18 H, $CH_3Si$ methyl). $^{13}C\{^1H\}$ NMR ($C_6D_6$): δ 86.9 (t, $^1J_{PC}$=156.0 Hz, 1 C PCP carbene), 40.3 (m, 4 C, CH-Cy, methine), 26.8 (m, 8 C, ortho Cy), 26.6 (s, 4 C, para Cy), 26.3 (s, 4 C, meta Cy), 26.1 (s, 4 C, meta Cy), 3.4 (s, 6 C, $CH_3Si$). $^{13}C\{^1H, ^{31}P\}$ NMR ($C_6D_6$): δ 86.9 (s, 1 C, PCP carbene), 40.3 (s, 4 C, CH-Cy, methine), 26.9 (s, 4 C, ortho Cy), 26.8 (s, 4 C, ortho Cy), 26.6 (s, 4 C, para Cy), 26.3 (s, 4 C, meta Cy), 26.1 (s, 4 C, meta Cy), 3.4 (s, 6 C, $CH_3Si$). $^{31}P\{^1H\}$ NMR ($C_6D_6$): δ 35.5 (2 P). Analysis calculated for $C_{31}H_{62}Cl_2N_2P_2Si_2Zr$: C, 50.11; H, 8.41; N, 3.77. Found: C, 49.97; H, 8.68; 3.63.

Preparation of [$ZrCl_2\{C(Ph_2P=NSiMe_3)_2\}$]

[$ZrCl_2\{N(SiMe_3)_2\}_2$] {literature preparation: Andersen, R. A. Inorg. Chem. 1979, 18, 1724–1725} (1.0 g, 2.07 mmol) was dissolved in 20 mL of toluene by stirring. The bisimine ligand, $CH_2(Ph_2P=NSiMe_3)_2$, (1.16 g, 2.08 mmol) was added as a solid to the solution which was then heated to reflux at 130° C. for 24 hours. The resultant pale yellow solution was concentrated to nearly 5 mL and mixed with 5 mL of hexane. Upon cooling overnight, a pale yellow crystalline solid was obtained which was isolated by filtration (Yield: 1.05 g, 70.5%). IR (Nujol mull): 1653 w, 1480 w, 1462 m, 1436 s, 1378 w, 1304 s, 1251 s, 1179 w, 1156 w, 1112 s, 1061 s, 1042 s, 1026 m, 999 w, 842 s, 785 m, 771 w, 753 w, 747 w, 737 w, 714 s, 695 s, 652 s, 631 m, 613 s, 571 m, 522 s. $^1$H NMR ($C_6D_6$): δ 7.6 (m, phenyl), 6.98 (m, phenyl), 6.92 (m, phenyl), 6.90 (m, phenyl), 0.25 (s, 18 H, $CH_3Si$ methyl). $^{13}C\{^1H\}$ NMR ($C_6D_6$): δ 134.2 (m, 4 C, ipso phenyl), 131.5 (t, $^2J_{PC}$=6.0 Hz, 8 C, ortho phenyl), 131.2 (s, 4 C, para phenyl), 128.5 (t, $^3J_{PC}$=6.2 Hz, 8 C, meta phenyl), 101.7 (t, $^1J_{PC}$=146 Hz, 1 C, PCP carbene), 2.6 (s, 6 C, $CH_3Si$). $^{13}C\{^1H, ^{31}P\}$ NMR ($C_6D_6$): δ 134.2 (s, 4 C, ipso phenyl), 131.5 (s, 8 C, ortho phenyl), 131.2 (s, 4 C, para phenyl), 128.5 (s, 8 C, meta phenyl), 101.7 (s, 1 C, PCP carbene), 2.6 (s, 6 C, $CH_3Si$). $^{31}P\{^1H\}$ NMR ($C_6D_6$): δ 15.7 (2 P). Analysis calculated for $C_{31}H_{38}Cl_2N_2P_2Si_2Zr$: C, 51.79; H, 5.33; N, 3.90. Found: C, 51.41; H, 5.78; N, 3.80.

Preparation of $ZrCl_2\{C(Ph_2P=NSiMe_3)_2\}$ Method B

To a suspension of $ZrCl_4(THF)_2$ (0.13 g, 0.35 mmol) in diethyl ether (5 mL) the dilithium salt $Li_2C(Ph_2P=NSiMe_3)_2$ 3 (0.20 g, 0.35 mmol) was added with stirring at room temperature. The mixture was stirred at room temperature for 2 days. Diethyl ether was removed and the resultant solid product was extracted with 5 mL of toluene and filtered to remove LiCl. The toluene solution was then concentrated to half the initial volume and the solution cooled to –15° C. for 2 days whereupon colorless crystals of $\{ZrCl_2\{C(Ph_2P=NSiMe_3)_2\}$ precipitated (Yield: 0.16 g, 63.5%). All spectroscopic and analytical data indicated that the product was identical with the compound identified as $\{ZrCl_2\{C(Ph_2P=NSiMe_3)_2\}$ as described above.

Preparation of [$HfCl_2\{C(Cy_2P=NSiMe_3)_2\}$]

[$HfCl_2\{N(SiMe_3)_2\}_2$] (0.2 g, 0.35 mmol) {literature preparation: Andersen, R. A. Inorg. Chem. 1979, 18, 1724–1725} was dissolved in 10 mL of toluene and solid bisimine ligand, $CH_2(Cy_2P=NSiMe_3)_2$ (0.204 g, 0.35 mmol) added to the solution with stirring. The resultant colorless solution was then heated at 140° C. for seven days. The final pale yellow solution was then concentrated and cooled to –15° C. for 24 hours to yield colorless crystals which were isolated by filtration (Yield: 0.21 g, 72.1%). IR (Nujol mull): 1447 s, 1404 w, 1377 w, 1356 w, 1320 s, 1297 w, 1260 s, 1246 s, 1202 w, 1192 w, 1176 w, 1168 w, 1112 m, 1024 b.s, 915 w, 887 m, 836 b.s, 783 m, 771 s, 754 s, 747 s, 707 w, 679 m, 654 s, 635 m, 615 s, 552 s, 542 m, 495 m, 485 m, 464 w. $^1$H NMR ($C_6D_6$): δ 2.1–1.1 (b. m, 40 H, $CH_2$-Cy methylene & 4 H, CH-Cy methine), 0.47 (s, 18 H, $CH_3Si$ methyl). $^{13}C\{^1H\}$ NMR ($C_6D_6$): δ 66.6 (t, $^1J_{PC}$=158.0 Hz, 1 C, PCP carbene), 40.7 (m, 4 C, CH-Cy, methine), 26.8 (m, 8 C, ortho Cy), 26.6 (s, 4 C, para Cy), 26.4 (s, 4 C, meta Cy), 26.3 (s, 4 C, meta Cy), 3.5 (s, 6 C, $CH_3Si$). $^{13}C\{^1H, ^{31}P\}$ NMR ($C_6D_6$): δ 66.6 (s, 1 C, PCP carbene), 40.7 (s, 4 C, CH-Cy, methine), 26.9 (s, 4 C, ortho Cy), 26.8 (s, 4 C, ortho Cy), 26.6 (s, 4 C, para Cy), 26.4 (s, 4 C, meta Cy), 26.3 (s, 4 C, meta Cy), 3.5 (s, 6 C, $CH_3Si$). $^{31}P\{^1H\}$ NMR ($C_6D_6$): δ 32.6 (2 P). Analysis calculated for $C_{31}H_{62}Cl_2HfN_2P_2Si_2$: C, 44.84; H, 7.53; N, 3.37. Found: C, 45.04; H, 7.98; N, 3.29.

Preparation of [$HfCl_2\{C(Ph_2P=NSiMe_3)_2\}$]

[$HfCl_2\{N(SiMe_3)_2\}_2$] (0.104 g, 0.18 mmol) {literature preparation: Andersen, R. A. Inorg. Chem. 1979, 18, 1724–1725} was dissolved in 10 mL of toluene to which was added solid bisimine ligand, $CH_2(Ph_2P=NSiMe_3)_2$ (0.102 g, 0.18 mmol). The solution was heated at 140° C. for 3 days, then concentrated to a small volume and layered with hexane, standing at room temperature for 2 days yielded colorless crystals which were isolated by filtration (Yield: 0.11 g, 74.8%). IR (Nujol mull): 1589 w, 1574 w, 1480 w, 1463 m, 1436 s, 1378 m, 1311 s, 1251 s, 1181 w, 1156 w, 1111 s, 1070 m, 1057 s, 1037 s, 999 m, 843 s, 787 s, 772 m, 754 m, 738 m, 716 s, 696 s, 654 s, 631 m, 622 s, 615 m, 576 m, 524 s. $^1$H NMR ($C_6D_6$): δ 7.63 (m, phenyl), 6.97 (m, phenyl), 6.91 (m, phenyl), 0.22 (s, 18 H, $CH_3Si$ methyl). $^{13}C\{^1H\}$ NMR ($C_6D_6$): δ 134.7 (m, 4 C, ipso phenyl), 131.5 (t, $^2J_{PC}$=6.0 Hz, 8 C, ortho phenyl), 131.0 (s, 4 C, para phenyl), 128.5 (t, $^3J_{PC}$=5.6 Hz, 8 C, meta phenyl), 84.6 (t, $^1J_{PC}$=145 Hz, 1 C, PCP carbene), 2.6 (s, 6 C, $CH_3Si$). $^{13}C\{^1H, ^{31}P\}$ NMR ($C_6D_6$): δ 134.7 (s, 4 C, ipso phenyl), 131.5 (s, 8 C, ortho phenyl), 131.0 (s, 4 C, para phenyl), 128.5 (s, 8 C, meta phenyl), 84.6 (s, 1 C, PCP carbene), 2.6 (s, 6 C, $CH_3Si$). $^{31}P\{^1H\}$ NMR ($C_6D_6$): δ12.2 (2 P). Analysis calculated for $C_{31}H_{38}Cl_2HfN_2P_2Si_2$ (0.5 toluene): C, 48.62; H, 4.97; N, 3.29. Found: C, 48.24; H, 5.21; N, 3.34.

Preparation of [Zr{C(Ph$_2$P=NSiMe$_3$)$_2$}(CH$_2$C$_6$H$_5$)$_2$]

[Zr(CH$_2$C$_6$H$_5$)$_4$] (1.0 g, 2.19 mmol) {literature preparation: Zucchini, U.; Albizzati, E.; Giannini, U. *J. Organomet. Chem.* 1971, 26, 357–372.} was added to 15 mL of toluene and stirred at room temperature. To the pale yellow brown suspension was added solid bisimine ligand, CH$_2$(Ph$_2$P=NSiMe$_3$)$_2$ (1.226 g, 2.19 mmol) at room temperature. The reaction mixture was stirred at room temperature for 2 days during which time a pale brown microcrystalline solid precipitated. The product was isolated by filtration, washed with few mL of hexane and dried (Yield: 1.34 g, 73.5%). IR (Nujol mull): 1900–1650 w, 1591 m, 1488 m, 1481 m, 1466 m, 1436 m, 1378 m, 1334 w, 1283 s, 1260 s, 1249 s, 1216 m, 1204 m, 1173 m, 1151 w, 1110 s, 1016 b.s, 971 m, 880 w, 834 b.s, 793 w, 776 s, 764 m, 743 s, 734 m, 720 s, 693 s, 656 s, 620 m, 614 m, 562 s. $^1$H NMR (C$_6$D$_6$): δ 7.34 (m, phenyl), 7.26 (m, phenyl), 7.24 (m, phenyl), 7.02 (m, phenyl), 6.93 (m, phenyl), 2.62 (s, 4 H, CH$_2$Ph methylene), 0.09 (s, 18 H, CH$_3$Si methyl). $^{13}$C {$^1$H} NMR (C$_6$D$_6$): δ 147.7 (s, 2 C, ipso benzyl), 135.9 (m, 4 C, ipso phenyl), 131.6 (t, $^2J_{PC}$=6.0 Hz, 8 C, ortho phenyl), 130.5 (s, 4 C, ortho benzyl), 128.9 (s, 4 C, meta benzyl), 128.2 (t, $^3J_{PC}$=6.5 Hz, 8 C, meta phenyl), 126.8 (s, 4 C, para phenyl), 121.2 (s, 2 C, para benzyl), 84.7 (t, $^1J_{PC}$=164 Hz, 1 C, PCP carbene), 68.8 (s, 2 C, CH$_2$Ph methylene), 3.6 (s, 6 C, CH$_3$Si). $^{13}$C {$^1$H, $^{31}$P} NMR (C$_6$D$_6$): δ 147.7 (s, 2 C, ipso benzyl), 135.9 (s, 4 C, ipso phenyl), 131.6 (s, 8 C, ortho phenyl), 130.5 (s, 4 C, ortho benzyl), 128.9 (s, 4 C, meta benzyl), 128.2 (s, 8 C, meta phenyl), 126.8 (s, 4 C, para phenyl), 121.2 (s, 2 C, para benzyl), 84.7 (s, 1 C, PCP carbene), 68.8 (s, 2 C, CH$_2$Ph methylene), 3.6 (s, 6 C, CH$_3$Si). $^{31}$P{$^1$H} NMR (C$_6$D$_6$): δ 12.4 (2 P). Analysis calculated for C$_{45}$H$_{52}$N$_2$P$_2$Si$_2$Zr: C, 65.10; H, 6.31; N, 3.37. Found: C, 65.65; H, 6.03; N, 3.31.

Preparation of [TiCl$_2${C(Ph$_2$P=NSiMe$_3$)$_2$}]

To a suspension of TiCl$_4$(THF)$_2$ (0.12 g, 0.35 mmol) in diethyl ether (10 ml) the dilithium salt Li$_2$C(Ph$_2$P=NSiMe$_3$)$_2$ (0.20 g, 0.35 mmol) was added with stirring at room temperature. The mixture was stirred at room temperature for 2 days. Diethyl ether was removed and the resultant yellow solid product was extracted with 8 mL of toluene and filtered to remove LiCl. The toluene solution was then concentrated to half and added 5 mL of hexane. Yellow crystalline compound obtained at room temperature over a period of one day. The product was filtered and dried in vacuum. Yield (0.13 g, 54.1%). IR data (Nujol Mull): 1437m, 1296m, 1250m, 1112s, 1079m, 1062s, 1026w, 999w, 843s, 782m, 745w, 721m, 714m, 695m, 652m, 636w, 610m, 569w, 523s. $^1$H NMR (C$_6$D$_6$): δ 7.62 (m, phenyl), 7.00 (m, phenyl), 6.92 (m, phenyl), 6.93 (m, phenyl), 0.37 (s, 18 H, CH$_3$Si methyl). $^{13}$C {$^1$H} NMR (C$_6$D$_6$): δ 191.0 (t, $^1J_{PC}$=145 Hz, 1 C, PCP carbene), 132.7 (m, 4 C, ipso phenyl), 132.0 (t, $^2J_{PC}$=6.2 Hz, 8 C, ortho phenyl), 131.6 (s, 4 C, para phenyl), 128.6 (t, $^3J_{PC}$=6.2 Hz, 8 C, meta phenyl), 3.1 (s, 6 C, CH$_3$Si). $^{31}$P{$^1$H} NMR (C$_6$D$_6$): δ 12.61 (2 P). Analysis calculated for C$_{31}$H$_{38}$Cl$_2$N$_2$P$_2$Si$_2$Ti: C, 55.11; H, 5.67; N, 4.15. Found: C, 53.93; H, 5.45; N, 3.84.

Preparation of [Sm{C(Ph$_2$P=NSiMe$_3$)$_2$—(NCy$_2$)(THF)]

To a toluene (4 mL) solution of [Sm(NCy$_2$)$_3$(THF)] (0.205 g, 0.268 mmol), H$_2$C(Ph$_2$P=NSiMe$_3$)$_2$ (0.15 g, 0.268 mmol) was added with stirring at room temperature. The reaction mixture was stirred at room temperature for a day and then refluxed for 30 minutes. Cooling the solution to room temperature and allowing the flask to stand for two days gave bright yellow crystals which were isolated by filtration. The crystals were dried under vacuum. Yield: 0.14 g, 54.4%. IR data (Nujol Mull): 1435s, 1341w, 1243s, 1177w, 1146m, 1107s, 1086s, 1065s, 1026s, 948m, 917w, 886m, 834s, 763s, 749s, 729m, 713s, 699s, 678w, 659m, 648m, 608s, 548s, 521s, 511s, 480s. $^{31}$P{$^1$H} NMR (C$_6$D$_6$): δ 43.3 (br.s). Analysis calculated for C$_{47}$H$_{68}$N$_3$OP$_2$Si$_2$Sm: C, 58.83; H, 7.14; N, 4.38. Found: C, 59.39; H, 7.25; N, 4.40.

What is claimed is:

1. A complex dilithium salt of the formula II:

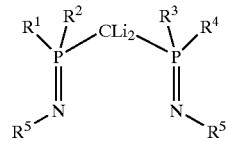

wherein R$^1$, R$^2$, R$^3$ and R$^4$ are independently selected from the group consisting of a hydrogen atom, a saturated and unsaturated straight chained, branched and cyclic hydrocarbyl radical which are unsubstituted or substituted by one or more substituents selected from the group consisting of a halogen atom and a C$_{1-6}$ alkyl radical; and each R$^5$ is independently selected from the group consisting of radicals selected from the group consisting of saturated and unsaturated straight chained, branched and cyclic hydrocarbyl radicals; radicals of the formula Si(R$^6$)$_3$ wherein each R$^6$ is independently selected from the group consisting of saturated or unsaturated straight chained, branched or cyclic hydrocarbyl radicals, radicals of the formula III:

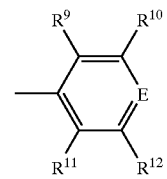

wherein R$^9$, R$^{10}$, R$^{11}$ and R$^{12}$ are independently selected from the group consisting of a hydrogen atom, a fluorine atom, a NO$_2$ radical, a C$_{1-6}$ alkyl radical, and a C$_{8-12}$ aryl radical and E is an endocyclic nitrogen atom or a C—CN group.

2. The complex according to claim 1, wherein R$^1$, R$^2$, R$^3$ and R$^4$ are selected from the group consisting of C$_{1-10}$ straight chained, branched or cyclic alkyl radicals which are unsubstituted or substituted by up to three substituents selected from the group consisting of a chlorine atom, a fluorine atom, C$_{1-4}$ alkyl radicals, and C$_{5-14}$ aromatic radicals which are unsubstituted or further substituted by up to n−1, wherein n is the number of carbon atoms in the aromatic radical substituents selected from the group consisting of a fluorine atom, a chlorine atom and a C$_{1-6}$ alkyl radical or an amido radical which is unsubstituted or substituted by up to two C$_{1-6}$ alkyl radicals.

3. The complex according to claim 2, wherein R$^1$, R$^2$, R$^3$ and R$^4$ are selected from the group consisting of a hydrogen atom, a fluorine atom, a chlorine atom, a methyl radical, an ethyl radical, a propyl radical, a butyl radical, a tertiary butyl radical and a phenyl radical.

4. The complex according to claim 3, wherein R$^5$ is the radical —Si(R$^6$)$_3$ and R$^6$ is selected from the group consisting of C$_{1-6}$ alkyl radicals.

5. The complex according to claim 3, wherein $R^5$ is a radical of the formula III:

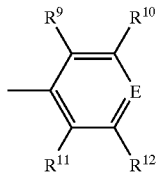

wherein $R^9$, $R^{10}$, $R^{11}$ and $R^{12}$ are independently selected from the group consisting of a hydrogen atom, a fluorine atom, a $NO_2$ radical, a $C_{1-6}$ alkyl radical, and a $C_{8-12}$ aryl radical and E is an endocyclic nitrogen atom or a C—CN group.

6. The complex according to claim 5, wherein E is an endocyclic nitrogen atom.

7. The complex according to claim 6, wherein E is a C—CN group.

8. The complex according to claim 7 wherein $R^5$ is a 4-cyanotetrafluorophenyl radical.

9. The complex according to claim 3, wherein $R^5$ is selected from the group consisting of a $C_{1-8}$ straight or branched alkyl radical and a $C_{6-12}$ cyclic aliphatic or aromatic radical.

10. The complex according to claim 9, wherein $R^5$ is selected from the group consisting of methyl, ethyl, butyl, phenyl and adamantyl radicals.

11. A process for preparing a complex having the formula:

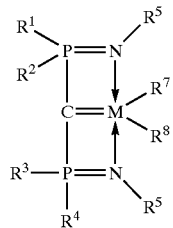

wherein $R^1$, $R^2$, $R^3$, $R^4$, $R^5$, are as defined below; and $R^7$ and $R^8$ are independently selected from the group consisting of a hydrogen atom, a halogen atom, an amide —$NR^1R^2$, imide =$NR^1$, alkoxide or aryl oxide group —$OR^1$, and an —OSi $(R^1)_3$ group where $R^1$ and $R^2$ are defined below and a saturated or unsaturated straight chained, branched or cyclic hydrocarbyl radical which are unsubstituted or substituted by a halogen atom or a $C_{1-6}$ alkyl radical and a Lewis base selected from the group $C_{1-6}$ alkyl ethers, $C_{4-8}$ cyclic ethers, $C_{1-6}$ tertiary amines, cyclic nitrogen aromatics compounds containing from 4 to 8 carbon atoms, and tertiary $C_{1-10}$ phosphines comprising either:

(A) reacting a compound of the formula I:

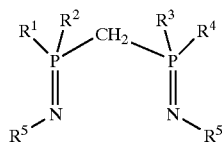

wherein $R^1$, $R^2$, $R^3$, $R^4$ are independently selected from the group consisting of a hydrogen atom, $C_{1-10}$ straight chained, branched or cyclic alkyl radicals which are unsubstituted or substituted by up to three substituents selected from the group consisting of a chlorine atom, a fluorine atom, $C_{1-4}$ alkyl radicals, and $C_{5-14}$ aromatic radicals which are unsubstituted or further substituted by up to n–1, wherein n is the number of carbon atoms in the aromatic radical substituents selected from the group consisting of a fluorine atom, a chlorine atom and a $C_{1-6}$ alkyl radical or an amido radical which is unsubstituted or substituted by up to two $C_{1-6}$ alkyl radicals and each $R^5$ is independently selected from the group consisting of radicals selected from the group consisting of saturated and unsaturated straight chained, branched and cyclic hydrocarbyl radicals; radicals of the formula $Si(R^6)_3$ wherein each $R^6$ is independently selected from the group consisting of saturated or unsaturated straight chained, branched or cyclic hydrocarbyl radicals; and radicals of the formula III:

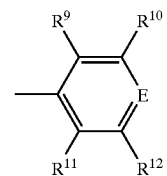

wherein $R^9$, $R^{10}$, $R^{11}$ and $R^{12}$ are independently selected from the group consisting of a hydrogen atom, a fluorine atom, a $NO_2$ radical, a $C_{1-6}$ alkyl radical, and a $C_{8-12}$ aryl radical and E is an endocyclic nitrogen atom or a C—CN group, with a compound of the formula $M(X)_s(Y)_t(L)_n$ wherein M is a metal atom selected from the group consisting of transition metal, lanthanides and group 11 and 12 post transition metals, X and Y are independently selected from a group consisting of an alkyl, preferably having from 1 to 10 carbon atoms which is unsubstituted or substituted by a $C_{1-4}$ alkyl radical or a $C_{6-10}$ aryl radical, a silylated amido or imido complex —$N(Si(R^6)_3)_2$ or =$N(Si(R^6))$ respectively, or imido =NR radicals where R is a $C_{1-10}$ alkyl or a $C_{6-10}$ aryl radical, Y is selected from the group consisting of a halogen atom, alkoxy radicals having from 1 to 10 carbon atoms and aryloxy radicals having from 6 to 10 carbon atoms, and the sum of s and t equal the valence of the transition metal M and provided that at least two of the X and Y groups can be eliminated from the compound, L is a Lewis base and n is from 0 to 3, in a $C_{5-12}$ hydrocarbyl solvent or a $C_{2-10}$ ether solvent at a temperature from 20° C. to 150° C.; or (B) reacting a compound of the formula II:

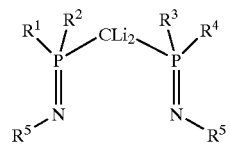

wherein $R^1$, $R^2$, $R^3$, $R^4$ and $R^5$ are as defined above, with a compound of the formula $M(X)_s(Y)_t(L)_n$ wherein M, X, Y, L, s, t and n are as defined above in a $C_{5-12}$ hydrocarbyl solvent or a $C_{2-10}$ ether solvent at a temperature from 20° C. to 150° C.

12. The process of claim 11, wherein a compound of formula I is reacted.

13. The process according to claim 12, wherein $R^1$, $R^2$, $R^3$ and $R^4$ are selected from the group consisting of $C_{1-10}$ straight chained, branched or cyclic alkyl radicals which are unsubstituted or substituted by up to three substituents selected from the group consisting of a chlorine atom, a fluorine atom, $C_{1-4}$ alkyl radicals, and $C_{5-14}$ aromatic radicals which are unsubstituted or further substituted by up to n-1, wherein n is the number of carbon atoms in the aromatic radical substituents selected from the group consisting of a fluorine atom, a chlorine atom, $C_{1-6}$ alkyl radicals, and an amido radical which is unsubstituted or substituted by up to two $C_{1-6}$ alkyl radicals.

14. The process according to claim 13, wherein the solvent is selected from the group consisting of pentene, hexane, heptene, octane, cyclohexane, methyl cyclohexane, benzene, toluene, xylene, hydrogenated naphtha, diethyl ether and diglyme.

15. The process according to claim 14, wherein $R^5$ is the radical —Si$(R^6)_3$ and $R^6$ is selected from the group consisting of $C_{1-6}$ alkyl radicals.

16. The process according to claim 15, wherein $R^5$ is a radical of the formula III:

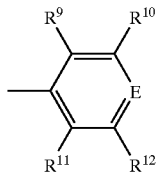

wherein $R^9$, $R^{10}$, $R^{11}$ and $R^{12}$ are independently selected from the group consisting of a hydrogen atom, a fluorine atom, a $NO_2$ radical, a $C_{1-6}$ alkyl radical, and a $C_{8-12}$ aryl radical and E is an endocyclic nitrogen atom or a C—CN group.

17. The process according to claim 16, wherein E is an endocyclic nitrogen atom.

18. The process according to claim 16, wherein E is a C—CN group.

19. The complex according to claim 16, wherein $R^5$ is a 4-cyanotetrafluorophenyl radical.

20. The process according to claim 14, wherein $R^5$ is selected from the group consisting of a $C_{1-8}$ straight or branched alkyl radical and a $C_{6-12}$ cyclic aliphatic or aromatic radical.

21. The process according to claim 16, wherein $R^5$ is selected from the group consisting of methyl, ethyl, butyl, phenyl and adamantyl radicals.

22. The process according to claim 11, wherein a compound of formula II is reacted.

23. The process according to claim 22, wherein $R^1$, $R^2$, $R^3$ and $R^4$ are selected from the group consisting of $C_{1-10}$ straight chained, branched or cyclic alkyl radicals which are unsubstituted or substituted by up to three substituents selected from the group consisting of a chlorine atom, a fluorine atom, $C_{1-4}$ alkyl radicals, and $C_{5-14}$ aromatic radicals which are unsubstituted or further substituted by up to n-1, wherein n is the number of carbon atoms in the aromatic radical substituents selected from the group consisting of a fluorine atom, a chlorine atom, $C_{1-6}$ alkyl radicals, and an amido radical which is unsubstituted or substituted by up to two $C_{1-6}$ alkyl radicals.

24. The process according to claim 23, wherein the solvent is selected from the group consisting of pentene, hexane, heptene, octane, cyclohexane, methyl cyclohexane, benzene, toluene, xylene, hydrogenated naphtha, diethyl ether and diglyme.

25. The process according to claim 24, wherein $R^5$ is the radical —Si$(R^6)_3$ and $R^6$ is selected from the group consisting of $C_{1-6}$ alkyl radicals.

26. The process according to claim 24, wherein $R^5$ is a radical of the formula III:

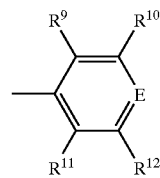

wherein $R^9$, $R^{10}$, $R^{11}$ and $R^{12}$ are independently selected from the group consisting of a hydrogen atom, a fluorine atom, a $NO_2$ radical, a $C_{1-6}$ alkyl radical, and a $C_{8-12}$ aryl radical and E is an endocyclic nitrogen atom or a C—CN group.

27. The process according to claim 26, wherein E is an endocyclic nitrogen atom.

28. The process according to claim 26, wherein E is a C—CN group.

29. The complex according to claim 26, wherein $R^5$ is a 4-cyanotetrafluorophenyl radical.

30. The process according to claim 24, wherein $R^5$ is selected from the group consisting of a $C_{1-8}$ straight or branched alkyl radical and a $C_{6-12}$ cyclic aliphatic or aromatic radical.

31. The process according to claim 30, wherein $R^5$ is selected from the group consisting of methyl, ethyl, butyl, phenyl and adamantyl radicals.

32. A process for alkylating or alkyoxylating a complex of the formula:

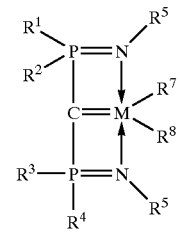

wherein $R^1$, $R^2$, $R^3$, $R^4$ are independently selected from the group consisting of a hydrogen atom, a saturated or unsaturated straight chained, branched or cyclic hydrocarbyl radical which is unsubstituted or substituted by one or more substituents selected from the group consisting of a halogen atom and $C_{1-6}$ alkyl radical and each $R^5$ is independently selected from the group consisting of radicals selected from the group consisting of saturated and unsaturated straight chained, branched and cyclic hydrocarbyl radicals; radicals of the formula Si$(R^6)_3$ wherein each $R^6$ is independently selected from the group consisting of saturated or unsaturated straight chained, branched or cyclic hydrocarbyl radicals; and radicals of the formula III:

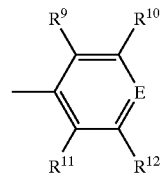

wherein $R^9$, $R^{10}$, $R^{11}$ and $R^{12}$ are independently selected from the group consisting of a hydrogen atom, a fluorine atom, a $NO_2$ radical, a $C_{1-6}$ alkyl radical, and a $C_{8-12}$ aryl radical and E is an endocyclic nitrogen atom or a C—CN group, and at least one $R^7$ and $R^8$ is a halogen and the other is a Lewis Base selected from the group consisting of $C_{1-6}$ alkyl ether, $C_{4-8}$ cyclic ethers, $C_{1-6}$ tertiary amines, cyclic nitrogen aromatic compounds containing from 4 to 8 carbon atoms, and tertiary $C_{1-10}$ phosphines; comprising reacting the compound with a Grignard reagent or an alkylating or alkoxylating agent.

33. The process according to claim 32, wherein Grignard reagent has formula RMgX wherein R is a $C_{1-10}$ branched or straight chained alkyl or aromatic radical, and X is a halogen atom to fully or partially alkylate the complex.

34. The process according to claim 32, wherein the alkylating agent is LiR wherein R is a $C_{1-10}$ branched or straight chain alkyl or aromatic radical to fully or partially alkylate the complex.

35. The process according to claim 32, wherein the alkoxylating reagent is $M^2OR$ wherein $M^2$ is an alkali metal and R is a $C_{1-10}$ branched or straight chained alkyl or aromatic radical to fully or partially alkoxylate the complex.

* * * * *